United States Patent [19]
Merlen et al.

[11] Patent Number: 6,150,292
[45] Date of Patent: Nov. 21, 2000

[54] CATALYST FOR ISOMERIZING AROMATIC C8 CUTS

[75] Inventors: Elisabeth Merlen, Rueil Malmaison; Fabio Alario, Neuilly sur Seine, both of France

[73] Assignee: Institut Francais du Petrole, France

[21] Appl. No.: 09/217,196

[22] Filed: Dec. 22, 1998

[30] Foreign Application Priority Data

Dec. 22, 1997 [FR] France .................................. 97 16457

[51] Int. Cl.$^7$ ...................................................... B01J 29/06
[52] U.S. Cl. .............................. 502/66; 502/64; 502/73; 502/74; 502/78
[58] Field of Search ................................ 502/64, 66, 73, 502/74, 78

[56] References Cited

U.S. PATENT DOCUMENTS

| | | | |
|---|---|---|---|
| 3,751,502 | 8/1973 | Hayes et al. ............................. | 260/668 |
| 4,418,006 | 11/1983 | Kim et al. ................................ | 502/73 |
| 5,032,561 | 7/1991 | Onodera et al. ......................... | 502/66 |
| 5,089,459 | 2/1992 | Sato et al. ................................ | 502/66 |
| 5,227,557 | 7/1993 | Bouronville et al. ................... | 585/419 |
| 5,413,976 | 5/1995 | Takami et al. ........................... | 502/66 |
| 5,686,374 | 11/1997 | Nakaoka ................................ | 502/313 |
| 5,885,443 | 3/1999 | Bogdan et al. ......................... | 208/138 |
| 5,952,258 | 9/1999 | Saitoh et al. ............................ | 502/61 |
| 5,952,535 | 9/1999 | King et al. .............................. | 585/475 |

FOREIGN PATENT DOCUMENTS 196 41 149   4/1997   Germany .

*Primary Examiner*—Tom Dunn
*Attorney, Agent, or Firm*—Millen, White, Zelano & Branigan, P.C.

[57] ABSTRACT

The present invention relates to a process for isomerizing aromatic C8 cuts in the presence of a catalyst containing a mordenite which is slightly or not dealuminated and a binder. This mordenite is generally present at least in part in its acid form and its Si/Al atomic ratio is less than 20, preferably in the range 5 to 15, and more preferably in the range 5 to 10. The catalyst also contains at least one metal from group VIII of the periodic table, preferably selected from the group formed by palladium and platinum. Finally, the catalyst further contains at least one metal from group III of the periodic table, namely gallium, indium or thallium, preferably indium, and optionally at least one metal from group IV of the periodic table, namely germanium, tin or lead, preferably tin. The present invention also relates to the catalyst used in the isomerization process and to a process for its preparation.

10 Claims, No Drawings

CATALYST FOR ISOMERIZING AROMATIC C8 CUTS

SUMMARY OF THE INVENTION

The present invention relates to a process for isomerizing aromatic C8 cuts, i.e., hydrocarbon cuts containing 8 carbon atoms, in the presence of a catalyst containing a mordenite which is optionally slightly dealuminated and a binder. This mordenite is at least partially in its acid form, in an amount generally of 3% to 60%, preferably 5% to 40% by weight, and the binder, which is preferably alumina, is generally present in an amount of 40% to 97%, preferably 60% to 95% by weight. The Si/Al atomic ratio of the mordenite is less than 20, preferably in the range 5 to 15, and more preferably in the range 5 to 10. The catalyst also contains at least one metal from group VIII of the periodic table, preferably selected from the group formed by palladium and platinum, in an amount, expressed with respect to the catalyst, generally in the range 0.01% to 2% by weight, preferably in the range 0.05% to 1.0% by weight The element or elements can be deposited on the zeolite or on the binder, preferably selectively on the binder. Finally, the catalyst further contains at least one metal from group III of the periodic table, namely selected from gallium, indium and thallium, preferably indium. The catalyst can optionally also contain at least one metal from group IV of the periodic table, selected from germanium, tin and lead, preferably tin. The present invention also relates to a catalyst used for isomerizing C8 aromatic cuts and to a process for its preparation.

Zeolites used in processes for isomerizing aromatic C8 cuts include ZSM-5, used alone or mixed with other zeolites such as mordenite. Such catalysts have been described in U.S. Pat. Nos. 4,467,129 and 4,482,773 and European patent EP-B-0 138 617. Other catalysts are based on mordenite and have been described, for example, in U.S. Pat. Nos. 4,723, 051 and 4,665,258 and French patent FR-A-2 477 903. While the activity of ZSM-5 is excellent due to the size of its channels, mordenite is more active.

The lack of selectivity of mordenite can be attenuated by optimizing formulations and/or specific treatments as has been described, for example, in the Applicant's patent FR-A-2 691 914. Those techniques reduce dismutation side reactions.

Isomerization of xylenes to ethylbenzene requires the presence of a group VIII metal. Optimized formulations based on mordenite and a group VIII metal lead to catalysts with which side reactions remain non-negligible. As an example, naphthene ring opening which may or may not be followed by cracking can be cited. The development of more selective catalysts is thus of particular importance.

The Applicant has discovered that, surprisingly, a catalyst for isomerizing aromatic C8 cuts containing a mordenite zeolite with an Si/Al atomic ratio of less than 20, preferably in the range 5 to 15, more preferably in the range 5 to 10, at least one group VIII metal, preferably selected from the group formed by palladium and platinum, more preferably platinum, in an amount, expressed with respect to the catalyst, generally in the range 0.01% to 2%, preferably in the range 0.05% to 1.0% by weight, said catalyst further comprising at least one group III metal in an amount, expressed with respect to the catalyst, generally in the range 0.01% to 2%, preferably in the range 0.05% to 1.0% by weight, leads to substantially improved performances, mainly in terms of selectivity, with respect to catalysts comprising mordenite and at least one metal selected from group VIII for isomerizing aromatic C8 cuts.

The present invention thus provides a process for isomerization of aromatic C8 cuts in the presence of a catalyst comprising:

a support containing
- 3% to 60%, preferably 5% to 40% by weight with respect to the support, of at least one zeolite with a mordenite structure characterized in that its Si/Al molar ratio is less than 20, preferably in the range 5 to 15, more preferably in the range 5 to 10;
- in general, 40% to 97%, preferably 60% to 95% by weight with respect to the support, of at least one binder, preferably alumina;
- in general 0.01% to 2%, preferably 0.05% to 1.0% by weight with respect to the catalyst, of at least one metal from group VIII of the periodic table, preferably selected from the group formed by platinum and palladium, more preferably platinum;
- in general, 0.01% to 2%, preferably 0.05% to 1.0% by weight, with respect to the catalyst, of at least one metal from group III of the periodic table, preferably indium;
- optionally, 0.01% to 2%, preferably 0.05% to 1.0% by weight with respect to the catalyst, of at least one metal from group IV of the periodic table, preferably tin.

Any zeolite with a mordenite structure which is known to the skilled person is suitable for the present invention. Thus, for example, the zeolite used as a base to prepare the catalyst of the present invention is a "large pore" mordenite in its sodium form, or a "small pore" mordenite in its sodium form with the required specifications as regards the Si/Al ratio. Thus, in accordance with the present invention, the Si/Al ratio is less than 20, preferably in the range 5 to 15 and more preferably in the range 5 to 10. At least one ion exchange step can then be carried out in at least one solution of $NH_4NO_3$ to obtain a zeolite with a greater or lesser residual sodium content.

This zeolite constitutes part of the composition of the catalyst support in an amount of 3% to 60% by weight, preferably 5% to 40% by weight, the complement to 100% by weight consisting of the binder in the catalyst support.

The binder (or matrix) in the support for the catalyst of the present invention is generally selected from elements of the group formed by clays, magnesia, aluminas, silicas, titanium oxide, boron oxide, zirconia, aluminium phosphates, titanium phosphates, zirconium phosphates and silica aluminas. Coal can also be used. The binder is preferably alumina.

The metals can be introduced either all in the same manner or using different techniques, at any moment during the preparation, before or after forming, and in any order. Further, intermediate treatments such as calcining and/or reduction can be carried out in between depositing the different metals.

The present invention also concerns a process for preparing a catalyst which can be carried out using any method which is known to the skilled person. At least one element from group VIII is introduced into the support, preferably to the binder, before or after forming. In general, the matrix and zeolite are mixed followed by forming. Forming is generally followed by calcining, generally at a temperature in the range 250° C. to 600° C. At least one element from group VIII of the periodic table is introduced after calcining by deposit on the support, preferably selectively onto the binder. Said elements are preferably almost completely deposited on the binder in a manner known to the skilled person by controlling the parameters used during deposition, such as the nature of the precursor used to carry out deposition. Further, at least one element from group III and optionally at least one element from group IV are added. Elements from group VIII and groups III, and optionally group IV can be added separately or simultaneously in at least one unitary step. When at least one group III element and at least one optional group IV element are separately added, it is preferable that it/they is/are added prior to the group VIII element.

The group VIII elements are deposited on the pre-formed zeolite-matrix mixture using any technique which is known to the skilled person. Deposition is, for example, carried out by dry impregnation, excess impregnation or ion exchange. Any precursor is suitable for depositing these elements. As an example, anion exchange can be carried out using hexachloroplatinic acid and/or hexachloropalladic acid in the presence of a competing agent, for example hydrochloric acid.

At least one other metal selected from group III and optionally at least one metal selected from group IV are also introduced. Any deposition technique which is known to the skilled person and any precursors are suitable for introducing the supplemental metal.

One preferred method for preparing the catalyst of the invention consists of mixing the zeolite in a moist matrix gel (generally obtained by mixing at least one acid and a powdered matrix), for example alumina, for a period necessary to obtain good homogeneity of the paste obtained, namely for about ten minutes, then passing the paste through a die to form extrudates, for example with a diameter in the range 0.4 to 4 mm. Then after oven drying for a few minutes at 100° C. and after calcining, for example for two hours at 400° C., at least one element, for example indium, is deposited by impregnation with an excess of indium nitrate. This deposition is followed by calcining then the second metal, for example platinum, is deposited, for example by anion exchange with hexachloroplatinic acid in the presence of a competing agent (hydrochloric acid), deposition being followed by final calcining.

The platinum is generally introduced into the matrix in the form of chloroplatinic acid, but for any noble metal, ammoniacal compounds or compounds such as ammonium chloroplatinate, platinum dicarbonyl dichloride, hexahydroxyplatinic acid, palladium chloride, or palladium nitrate can be used.

Ammoniacal can, for example, be employed to make use in the present invention of at least one noble metal from the platinum group.

Examples in the case of platinum are platinum IV hexamine salts with formula $Pt(NH_3)_6X_4$; salts of platinum IV halogenopentamines with formula $(PtX(NH_3)_5)X_3$; salts of platinum N tetrahalogenodiamines with formula $PtX_4(NH_3)_2$; platinum complexes with halogen-polyketones and halogenated compounds with formula $H(Pt(aca)_2X)$; where X is a halogen selected from the group formed by chlorine, fluorine, bromine and iodine, preferably X is chlorine, and aca represents the residue with formula $C_5H_7O_2$ derived from acetylacetone.

Introducing the noble platinum group metal is preferably carried out by impregnating with an aqueous or organic solution of one of the organometallic compounds cited above. Suitable organic solvents are paraffinic hydrocarbons, naphthenic hydrocarbons or aromatic hydrocarbons, and also organic halogenated compounds containing, for example, 1 to 12 carbon atoms per molecule. Examples are n-heptane, methylcyclohexane, toluene and chloroform. Mixtures of solvents can also be used.

The group III metal and optional group IV metal can be introduced by means of compounds such as tin chlorides, bromides and nitrates, and indium nitrate and chloride.

The metal can also be introduced in the form of at least one organic compound selected from the group formed by complexes of said metal, in particular polyketone complexes of the metal and hydrocarbylmetals such as metal alkyls, cycloalkyls, aryls, alkylaryls and arylalkyls.

In the latter case, the metal is advantageously introduced using a solution of an organometallic compound of said metal in an organic solvent. Metal organohalogenated compounds can also be used. Particular metal compounds are triphenylindium for indium, and tetrabutyltin for tin.

The impregnating solvent is selected from the group formed by paraffinic hydrocarbons, naphthenic hydrocarbons or aromatic hydrocarbons containing 6 to 12 carbon atoms per molecule and halogenated organic compounds containing 1 to 12 carbon atoms per molecule. Examples are n-heptane, methylcyclohexane and chloroform. Mixtures of the above solvents can also be used.

It is also possible to introduce at least one group III metal and optionally at least one group IV metal before introducing at least one noble metal from the platinum group. If this metal is introduced before the noble metal, the metal compound used is generally selected from the group formed by the metal halide, nitrate, acetate, tartrate, carbonate and oxalate. Introduction is thus carried out in an aqueous solution. However, it can also be introduced using a solution of an organometallic compound of the metal. In this case, before proceeding to introduce at least one noble metal, calcining in air is carried out.

The catalyst of the invention is generally and preferably in the form of pellets, aggregates, extrudates or beads depending on its use.

Preparation of the catalyst is generally completed by a final calcining, normally at a temperature in the range 250° C. to 600° C., preferably preceded by drying, for example oven drying, at a temperature in the range from room temperature to 250° C., preferably in the range 40° C. to 200° C. The drying step is preferably carried out during the rise of temperature required to carry out the calcining step.

The present invention also relates to a catalyst for isomerizing an aromatic C8 cut, comprising a mordenite which is slightly or not dealuminated, at least partially in its acid form, with an Si/Al atomic ratio of less than 20, preferably in the range 5 to 15, and more preferably in the range 5 to 10, and a binder, at least one metal from group VIII of the periodic table in an amount, expressed with respect to the catalyst, in the range 0.01% to 2% by weight, preferably in the range 0.05% to 1.0% by weight, and also containing at least one metal from group III of the periodic table in an amount, expressed with respect to the catalyst, in the range 0.01% to 2.0% by weight, and optionally at least one metal from group IV of the periodic table in an amount, expressed with respect to the catalyst, in the range 0.01% to 2.0% by weight.

The feed introduced comprises, for example, either solely a mixture of xylenes, or a mixture of xylene(s) and ethylbenzene.

The process is generally carried out under the following operating conditions: a temperature in the range 240° C. to 600° C.; a pressure in the range 0.05 MPa to 10 MPa, preferably in the range 0.2 to 3 MPa; a space velocity, expressed in kilograms of feed introduced per kilogram of catalyst per hour, in the range 0.5 to 200 $h^{-1}$, preferably in the range 1 to 50 $h^{-1}$; and a molar ratio of hydrogen to hydrocarbon(s) in the range 0.5 to 20, preferably in the range 2 to 14.

The following examples illustrate the invention without in any way limiting its scope.

EXAMPLES

EXAMPLE 1
Preparation of Catalyst A, Not in Accordance with the Invention, Containing Mordenite and 0.3% by Weight of Platinum The starting zeolite was a mordenite with a Si/Al ratio of 5.2 and a unit cell of 2.794 nm$^3$. The zeolite underwent three ion exchange steps in a solution of 10 N NH$_4$NO$_3$ at about 100° C. over 4 hours. The solid obtained contained 25 ppm of sodium.

This zeolite was then formed by extrusion with an alumina gel to produce, after drying and calcining in dry air, a catalyst I1 which contained 25% by weight of mordenite zeolite in its hydrogen form and 75% of alumina.

This catalyst I1 underwent anion exchange with hexachloroplatinic acid in the presence of a competing agent (hydrochloric acid), to deposit 0.3% by weight of platinum with respect to the catalyst. The moist solid was then dried at 120° C. for 12 hours and calcined in a flow of dry air at 500° C. for one hour. Catalyst A obtained contained 24.9% by weight of mordenite in its hydrogen form, 74.8% of alumina and 0.28% of platinum.

EXAMPLE 2
Preparation of Catalyst B, in Accordance with the Invention, Containing a Mordenite, 0.3% by Weight of Platinum and 0.1% by Weight of Indium Indium was deposited on catalyst I1 by impregnation with an excess of indium nitrate to obtain about 0.1% by weight of indium. This deposition was followed by calcining then platinum was deposited by anion exchange with hexachloroplatinic acid in the presence of a competing agent (hydrochloric acid) to deposit 0.3% by weight of platinum with respect to the catalyst. The moist solid was then dried at 120° C. for 12 hours and calcined in a flow of dry air at a temperature of 500° C. for one hour. Catalyst B obtained contained 24.9% by weight of mordenite in its hydrogen form, 74.72% by weight of alumina, 0.29% of platinum and 0.09% of indium.

EXAMPLE 3
Preparation of Catalyst C, in Accordance with the Invention, Containing a Mordenite, 0.3% by Weight of Platinum, 0.1% by Weight of Indium and 0.1% by Weight of Tin Indium was deposited on catalyst I1 by impregnation with an excess of indium nitrate to obtain about 0.1% by weight of indium. This deposition was followed by calcining in air for 1 hour at 500° C. Tin was deposited by dry impregnation of tetrabutyltin to obtain about 0.1% by weight of tin. This deposition was followed by calcining in air for 1 hour at 500° C. then platinum was deposited by anion exchange with hexachloroplatinic acid in the presence of a competing agent (hydrochloric acid) to deposit 0.3% by weight of platinum with respect to the catalyst. The moist solid was then dried at 120° C. for 12 hours and calcined in a flow of dry air at a temperature of 500° C. for one hour. Catalyst C obtained contained 24.9% by weight of mordenite in its hydrogen form, 74.58% by weight of alumina, 0.31% of platinum, 0.11% of indium and 0.10% of tin.

EXAMPLE 4
Preparation of Catalyst D, Not in Accordance with the Invention, Containing a Mordenite with a Si/Al Ratio of 25, 0.31% by Weight of Platinum and 0.15% by Weight of Tin The starting material used was a mordenite zeolite with a global Si/Al atomic ratio of 10.0, and a weight content of sodium with respect to the weight of dry mordenite zeolite of about 2.8%.

This mordenite zeolite underwent acid attack using a solution of 2.5 N nitric acid with a V/W of 10 for 4 hours under reflux to partially extract the aluminium atoms present in the zeolitic framework of the mordenite. The dealuminated mordenite zeolite then underwent ion exchange in a 10 N NH$_4$NO$_3$ solution at about 100° C. for 4 hours to withdraw the residual sodium.

At the end of these treatments, the global Si/Al atomic ratio of the mordenite zeolite in its H form was 25, and the sodium content with respect to the dry mordenite zeolite was 52 ppm by weight.

This zeolite was then formed by extrusion with an alumina gel to produce, after drying and calcining in dry air, a catalyst I2 which contained 25% by weight of mordenite zeolite in its hydrogen form and 75% of alumina.

Tin was deposited on catalyst I2 by dry impregnation of tetrabutyltin to obtain about 0.15% by weight of tin. This deposition was followed by calcining in air for 1 hour at 500° C. then platinum was deposited by anion exchange with hexachloroplatinic acid in the presence of a competing agent (hydrochloric acid) to deposit 0.4% by weight of platinum with respect to the catalyst. The moist solid was then dried at 120° C. for 12 hours and calcined in a flow of dry air at a temperature of 500° C. for one hour. Catalyst D obtained contained 24.9% by weight of mordenite in its hydrogen form, 74.55% by weight of alumina, 0.39% of platinum and 0.16% of tin.

EXAMPLE 5
Evaluation of Catalytic Properties of Catalysts A, B, C and D When Isomerising an Aromatic C8 Cut The performances of catalysts A, B, C and D were evaluated for isomerization of an aromatic C8 cut. The operating conditions were as follows:

temperature: 390° C.;

pressure: 15 bars, (1 bar=0.1 MPa);

hydrogen/hydrocarbon molar ratio: 4

Catalysts A and C were pre-treated with a feed containing dimethyldisulfide (DMDS) at a concentration such that the sulfur/metal atomic ratio was 1.5. This treatment was carried out for 3 hours at 400° C.

The catalysts were compared in terms of activity by means of the ethylbenzene (EB) conversion and in terms of selectivity by means of net losses. Further, the side reactions were classified into three categories: hydrogenation, cracking and dismutation, and the relative proportions of these three types of reactions were compared.

TABLE 1

| Catalysts | A (not invention) | B (invention) | C (invention) | D (not invention) |
|---|---|---|---|---|
| EB conversion (%) | 60.7 | 60.5 | 59.7 | 58.9 |
| Net losses (wt %) | 9.3 | 6.0 | 6.2 | 8.9 |
| Side reactions (%) | | | | |
| hydrogenation | 62.3 | 72.0 | 67.4 | 62.6 |
| cracking | 17.4 | 7.0 | 6.8 | 9.7 |
| dismutation | 20.3 | 21.0 | 25.8 | 27.7 |
| Total | 100.0 | 100.0 | 100.0 | 100.0 |

An analysis of the proportions of the different side reactions shows a substantial gain when using catalyst B of the invention. The hydrogenation losses actually rose slightly but this drawback was minimized by the possibility of recycling. In contrast, losses due to cracking, which represent a net loss, were substantially reduced. This fell from 37.7% losses with catalyst A to 28% with catalyst B. More generally, the higher selectivity of catalyst B of the invention is shown by the production of net losses of 6%, much lower than that of catalyst A (9.3%). This performance illustrates the gains in selectivity obtained during use of the catalysts of the present invention.

Catalyst C of the invention had a slightly lower activity than that of catalyst A, not of the invention. Adding indium and tin substantially reduced the net losses. An analysis of the different side reactions shows that their distribution is substantially against cracking, in contrast to catalyst A, not of the invention, which caused the net losses, since losses by dismutation are more readily recoverable.

Catalyst D, not in accordance with the invention, had an ethylbenzene conversion which was lower than that obtained with catalysts B and C of the invention. Further, the catalysts are distinguished on the basis of net losses, i.e., losses by dismutation/transalkylation were higher in the case of catalyst D and represented 27.7% of the losses as against 21% in the case of catalyst B, and cracking losses were higher in the case of catalyst D and represented 9.7% of the losses in contrast with 6.8% of the losses in the case of catalyst C. The net losses changed from 6% and 6.2% by weight for catalysts B and C to 8.9% by weight for catalyst D. These performances also illustrate the gains in selectivity obtained during use of catalysts in accordance with the present invention.

In conclusion, the catalyst of the invention is more selective than prior art catalysts.

What is claimed is:

1. A catalyst comprising, with respect to the weight of catalyst:

0.01% to 2% of at least one group VIII metal;

0.01% to 2% of at least one group III metal;

the complement being a support, having deposited thereon said group VIII and group III metals, said support, containing, with respect to the support:

3% to 60% of at least one zeolite with a mordenite structure with an Si/Al molar ratio of less than 20 in admixture with 40% to 97% by weight of at least one binder.

2. A catalyst according to claim 1, comprising 0.01% to 2% of at least one group IV metal.

3. A catalyst according to claim 1, comprising 0.05 to 1.0% by weight of at least one group VIII metal; 0.05 to 1.0% by weight of at least one group III metal; 5 to 40% by weight of mordenite zeolite; and 60 to 95 % of binder.

4. A catalyst according to claim 1, wherein the zeolite has an Si/Al ratio of 5 to 15.

5. A process for preparing a catalyst according to claim 1 comprising:

producing a support by mixing a binder and a zeolite with a mordenite structure, forming the mixture, and calcining;

depositing at least one group VIII metal and at least one group III metal, and optionally at least one group IV metal, on the support, simultaneously or separately, by dry impregnation or by excess impregnation or by ion exchange, before or after forming the support; and calcining.

6. A process for preparing a catalyst according to claim 5, in which at least one group VIII metal and at least one group III metal and optionally at least one group IV metal are deposited on the binder.

7. A process according to claim 5, in which the precursor of at least one group III element and optionally at least one group IV element is a bromide, chloride, nitrate, polyketone complex, hydrocarbylmetal, organometallic compound or organohalogenated compound.

8. A catalyst produced by a process of claim 5.

9. A catalyst produced by a process of claim 6.

10. A catalyst produced by a process of claim 7.

* * * * *